United States Patent
Aperia et al.

(10) Patent No.: US 6,207,706 B1
(45) Date of Patent: Mar. 27, 2001

(54) USE OF COMT INHIBITORS FOR THE MANUFACTURE OF A MEDICAMENT FOR THE PREVENTION OF DIABETIC VASCULAR DYSFUNCTIONS

(75) Inventors: Anita Chatarina Aperia, Lidingö (SE); Inge-Britt Yvonne Lindén, Espoo (FI)

(73) Assignee: Orion-Yhtyma Oyj, Espoo (FI)

( * ) Notice: Subject to any disclaimer, the term of this patent is extended or adjusted under 35 U.S.C. 154(b) by 0 days.

(21) Appl. No.: 09/331,113

(22) PCT Filed: Dec. 19, 1997

(86) PCT No.: PCT/FI97/00812

§ 371 Date: Aug. 23, 1999

§ 102(e) Date: Aug. 23, 1999

(87) PCT Pub. No.: WO98/27973

PCT Pub. Date: Jul. 2, 1998

(30) Foreign Application Priority Data

Dec. 20, 1996 (GB) .................................................. 9626472

(51) Int. Cl.[7] .................................................. A61K 31/275
(52) U.S. Cl. ............................................. 514/519; 514/520
(58) Field of Search ...................................... 514/519, 520

(56) References Cited

U.S. PATENT DOCUMENTS

| | | | |
|---|---|---|---|
| 4,672,042 | 6/1987 | Ross, Jr. et al. ..................... 436/161 |
| 4,963,590 | 10/1990 | Bäckström et al. ................. 514/678 |
| 5,001,152 | * 3/1991 | Aho et al. ............................ 514/519 |
| 5,019,575 | 5/1991 | Haikala et al. ..................... 514/247 |
| 5,112,861 | 5/1992 | Bäckström et al. ................. 514/520 |
| 5,122,524 | 6/1992 | Haikala et al. ..................... 514/242 |
| 5,185,332 | 2/1993 | Haikala et al. .................... 514/222.5 |
| 5,185,370 | 2/1993 | Bäckström et al. ................. 514/520 |
| 5,236,952 | * 8/1993 | Bernauer et al. .................... 514/520 |
| 5,283,352 | 2/1994 | Bäckström et al. ................. 558/401 |
| 5,288,750 | 2/1994 | Pohto et al. ......................... 514/438 |
| 5,292,771 | 3/1994 | Bäckström et al. ................. 514/472 |
| 5,389,653 | * 2/1995 | Bernauer et al. .................... 514/535 |
| 5,446,194 | * 8/1995 | Backstrom et al. ................. 558/401 |
| 5,476,875 | * 12/1995 | Bernauer et al. .................... 514/676 |
| 5,489,614 | 2/1996 | Korkolainen et al. ............... 514/676 |

FOREIGN PATENT DOCUMENTS

| | | |
|---|---|---|
| 0 237 929 A1 | 9/1987 | (EP) . |
| 2 200 109 | 7/1988 | (GB) . |
| WO 96/37456 | 11/1996 | (WO) . |

OTHER PUBLICATIONS

Eklöf, A.–C. et al., "Natriuretic and Vasodilating Effects of Dopamine are Mimicked by Oral Administration of a Catechol–O–Methyltransferase (COMT) Inhibitor," *J. Am. Soc. Nephrology* 5:657, Abstract No. 23P (Oct., 1994).

Holtbäck, U. et al., "Regulators of Renal Dopamine Metabolism Control Salt Excretion," *J. Am. Soc. Nephrology* 7:1633, Abstract A1922 (Nov., 1996).

Kaakkola, S. et al., "General Properties and Clinical Possibilities of New Selective Inhibitors of Catechol O–methyltransferase," *Gen. Pharmac.* 25:813–824 (Sep., 1994).

Dialog File 351, Derwent WPI English language abstract for EP 0 237 929 (Doc. AL1).

* cited by examiner

*Primary Examiner*—Kevin E. Weddington
(74) *Attorney, Agent, or Firm*—Sterne, Kessler, Goldstein & Fox P.L.L.C.

(57) ABSTRACT

The invention is related to the use of COMT inhibitors in the treatment of diabetic vasculat dyfunctions.

13 Claims, No Drawings

USE OF COMT INHIBITORS FOR THE MANUFACTURE OF A MEDICAMENT FOR THE PREVENTION OF DIABETIC VASCULAR DYSFUNCTIONS

FIELD OF THE INVENTION

The invention relates to the use of catechol-O-methyl transferase (COMT) inhibitors in the prevention of diabetic vascular dysfunctions, preferably nephropathy, retinopathy and neuropathy.

BACKGROUND OF THE INVENTION

There is a world-wide search for a therapy that can prevent the complications in type 1 and type 2 diabetes. Chronic exposure to diabetes leads to an increased incidence of microangiopathic complications which are associated with considerable morbidity and mortality. For example, disturbances in the microcirculation of the feet may lead to amputation of the legs which in turn can cause severe complications. In the case of diabetic nephropathy renal failure is usually the actual cause of death. Diabetes is also the most common cause of renal failure among young adults.

The factors that lead to diabetic nephropathy have been extensively studied but are still incompletely known. According to the general concept, early functional effects of diabetes, such as hyperfiltration, are contributing factors. Hyperfiltration is associated with increased glomerular pressure and increased albumin excretion rate (AER). Increased AER is considered to be an early sign of glomerular damage.

The presently most commonly used therapy, ACE inhibitors, will not prevent the development of diabetic nephropathy, but may postpone the development of terminal renal failure.

It has been disclosed that nitecapone, a COMT inhibitor has a natriuretic effect (Eklöf et al. J. Am. Soc. Nephrology 5 (3), 657, 1994, Holtbäck et al., J. Am. Soc. Nephrology, 7(9), 1633, 1996). However, the effect of COMT inhibitors on hyperfiltration and albuminuria has not been suggested earlier.

SUMMARY OF THE INVENTION

The object of the invention is to provide the use of COMT inhibitors, especially nitecapone (3-(3,4-dihydroxy-5-nitrophenyl)methylene-2,4-pentanedione) in the the prevention of diabetic vascular dysfunctions, such as nephropathy, retinopathy and neuropathy. The compounds of the invention may be used for the treatment of any type of diabetes.

DETAILED DESCRIPTION OF THE PREFERRED EMBODIMENTS

Suitable COMT-inhibitors and methods for preparation thereof have been described, e.g. in GB 2200109, EP 237929 and PCT application PCT/FI96/00295.

The invention is directed to the use of COMT inhibitors or their pharmaceutically acceptable salts or esters in the manufacture of a medicament for use in the prevention of diabetic vascular dysfunctions, such as the prevention of dysfunctions related to microangiopathy; nephropathy and/or retinopathy; and the attenuation of albuminuria. A COMT inhibitor useful in this regard is nitecapone.

The invention is also directed to a method for the prevention of diabetic vascular dysfunctions by administering to a mammal in need of such prevention an effective amount of a COMT inhibitor or its pharmaceutically acceptable salt or ester to prevent said dysfunctions, such as the prevention of a dysfunction related to microangiopathy; nephropathy and/or retinopathy. A COMT inhibitor useful in this regard is nitecapone.

Pharmaceutically acceptable salts and esters of these compounds, when applicable, may be prepared by known methods. All physiologically acceptable salts are useful as active medicaments, however, sodium, potassium, ammonium, calcium and magnesium salts and salts with hydrochloric, hydrobromic, phosphoric and sulfuric acids and with organic acids like oxalic, fumaric, tartaric, malonic, acetic and citric acids etc. are preferred.

The effective dose of the compound varies considerably depending on the efficacy of the COMT-inhibitor in question, the severity of the condition to be treated, and the route of administration. Most preferred are oral formulations. The effective dose for human beings is likely to be from about 20 to 2000 mg per day.

The compounds according to this invention are given to a patient as such or in combination with one or more other active ingredients and/or suitable pharmaceutical non-active additives. The latter group comprises solvents, gel forming agents, emulsifiers, stabilizers, colorants, preservatives, lubricants, glidants, fillers and other widely used excipients and formulation aids.

The compounds used in this invention are formulated into dosage forms using commonly known pharmaceutical manufacturing methods. The dosage forms can be e.g. tablets, capsules, granules, suppositories, emulsions, suspensions or solutions. Depending on the route of administration and the galenic form, the concentration of the active compound in a formulation can typically vary between about 1 to 100 % (w/w).

Choosing the auxiliary ingredients for the formulation is routine for those of ordinary skill in the art. It is evident that suitable solvents, gel forming ingredients, dispersion forming ingredients, colors etc. are used in a normal way.

EXAMPLE 1

Results

The Effect of Nitecapone on Renal Function

The effect of nitecapone 3-(3,4-dihydroxy-5-nitrophenyl) methylene-2,4-pentanedione treatment (from 3 to 6 weeks) on renal function was tested in diabetic rats. Streptozocin (STZ) was injected into the tail vein of rats to induce diabetes. Blood glucose concentration was measured regularly. Hyperglycemia in diabetic rats to be included in the test had to be apparent 12 h after STZ injection and had to remain stable (16–25 mM glucose) throughout the whole observation time. STZ-administered rats with unfasting plasma glucose concentration <16.5 mM at 48 h after injection were excluded.

The effect of nitecapone on glomerular filtration rate (GFR) is given in Table 1. The rats were studied with conventional clearance techniques using inulin as an indicator of GFR. Values are given for age-matched control rats. The nontreated diabetic rats had a characteristic hyperfiltration, which was abolished by nitecapone treatment. GFR in diabetic nitecapone treated rats and control rats was not different.

TABLE 1

Effect of daily treatment with nitecapone (30 mg/kg bw BID) on GFR in rats with streptozotocin-induced diabetes (3 weeks)

|  | GFR ml/min |
|---|---|
| Diabetic rats without nitecapone | 2.25 +/− 0.26* |
| Diabetic rats with nitecapone | 1.28 +/− 0.26 |
| Non-diabetic rats | 1.59 +/− 0.12 | n = 7–8 in each group
*significantly different from other 2 group (ANOVA)

The effect of daily treatment with nitecapone on albumin excretion rate (AER) in diabetic rats is given in Table 2. The untreated diabetic rats had increased AER. Nitecapone treatment caused a pronounced attenuation of this diabetic complication. Almost 50% of the nitecapone treated rats had a very low (i.e. normal) AER.

TABLE 2

Effect of daily treatment with nitecapone (30 mg/kg bw BID) on albumin excretion rate (AER)

|  | AER, mg/ml GFR |
|---|---|
| 3 weeks without nitecapone | 6.18 +/− 1.53 |
| 3 weeks with nitecapone | 1.20 +/− 1.39* |
| 6 weeks without nitecapone | 10.9 +/− 2.33 |
| 6 weeks with nitecapone | 2.33 +/− 2.91* |

*significantly lower than in nontreated rats

In addition to the above identified results it was consistently observed that intestinal edema, which characteristically occurs in diabetic rats, was not present in the nitecapone treated animals.

It is also surprising how low doses of nitecapone are needed to obtain the desirable effect. This fact is shown by the results represented in Table 3. Nitecapone in drinking water (25 μg/ml water=9.7 mg/kg/day) was administered to Sprague Dawley rats with streptozotocin-induced diabetes for 10 days. The glomerular filtration rate was determined on day 10. The blood samples were taken on day 7 at 10 a.m.

TABLE 3

Effect of daily treatment with nitecapone (9.7 mg/kg in drinking water) on GFR in rats with streptozotocin-induced diabetes (10 days)

| Rat Nr | Treatm. | BW g | Water intake ml/day | GFR ml/min | NC in plasma ng/ml |
|---|---|---|---|---|---|
| 84A | CON | 281 | 140 | 3.36 | — |
| 84B | CON | 276 | 140 | 2.34 | — |
| 84C | CON | 276 | 140 | 3.31 | — |
| 85A | CON | 272 | 180 | 3.55 | — |
| 85B | CON | 256 | 180 | 3.87 | — |
|  |  | m 272 ± 4 | m 156 ± 10 | m 3.29 ± 0.3 |  |
| 92A | NC | 273 | 100 | 2.38 | 64 |
| 92B | NC | 289 | 100 | 2.42 | 58 |
| 92C | NC | 279 | 100 | ND | 65 |
| 93A | NC | 256 | 110 | 2.38 | 43 |
| 93B | NC | 269 | 110 | 2.87 | 29 |
| 93C | NC | 265 | 110 | 2.44 | 70 |

TABLE 3-continued

Effect of daily treatment with nitecapone (9.7 mg/kg in drinking water) on GFR in rats with streptozotocin-induced diabetes (10 days)

| Rat Nr | Treatm. | BW g | Water intake ml/day | GFR ml/min | NC in plasma ng/ml |
|---|---|---|---|---|---|
|  |  | m 272 ± 4 | m 105 ± 5 | m 2.50 ± 0.1 | m 55 ± 6 |

ND = not determined.
m = mean
± = se

EXAMPLE 2

The Effect of Nitecapone on Retinopathy

The ability of nitecapone to attenuate the biochemical markers associated with diabetic retinopathy was tested in cultured porcine retina pigment epithelium cells (RPE). The content of protein kinase C (PKC) was measured in the cells exposed to normal (5 mM) or high (20 or 50 mM) glucose concentrations with or without nitecapone. At the tested concentrations (10 to 40 μM) nitecapone abolished the glucose-induced increase in the PKC content in RPE cells. This suggests that nitecapone has an antiretinopathic effect.

What is claimed is:

1. A method for the treatment and/or prevention of diabetic vascular dysfunction, said method comprising administering to a mammal in need of said treatment and/or prevention an effective amount of a COMT inhibitor or its pharmaceutically acceptable salt or ester to treat and/or prevent said vascular dysfunction.

2. The method of claim 1, wherein said vascular dysfunction is microangiopathy.

3. The method of claim 1, wherein said vascular dysfunction is nephropathy.

4. The method of claim 1, wherein said vascular dysfunction is retinopathy.

5. The method of any one of claims 1–4, wherein said COMT inhibitor is nitecapone.

6. A method for the treatment and/or prevention of neuropathy by administering to a mammal in need of said treatment and/or prevention an effective amount of a COMT inhibitor or its pharmaceutically accept salt or ester to treat and/or prevent said neuropathy.

7. The method of claim 6, wherein said COMT inhibitor is nitecapone.

8. The method of claim 6 or claim 7 wherein said neuropathy is diabetic neuropathy.

9. The method of claim 1 wherein said diabetic vascular dysfunction is a dysfunction of type I diabetes.

10. The method of claim 1 wherein said diabetic vascular dysfunction is a dysfunction of type II diabetes.

11. The method of claim 1 wherein said vascular dysfunction is intestinal edema.

12. The method of claim 1 wherein said effective amount of said COMT inhibitor attenuates glucose induced increases in protein kinase C content in retina pigment epithelium cells.

13. The method of any one of claims 8–12 wherein said COMT inhibitor is nitecapone.

* * * * *